(12) United States Patent
Bowden et al.

(10) Patent No.: US 6,209,579 B1
(45) Date of Patent: Apr. 3, 2001

(54) LOW SUPPLY PRESSURE ALARM FOR GAS SUPPLY

(75) Inventors: Kevin D. J. Bowden, Orangeville; Helmut F Zauner, Stouffville, both of (CA)

(73) Assignee: O-Two Systems International Inc. (CA)

( * ) Notice: Subject to any disclaimer, the term of this patent is extended or adjusted under 35 U.S.C. 154(b) by 0 days.

(21) Appl. No.: 09/246,599

(22) Filed: Feb. 8, 1999

(51) Int. Cl.$^7$ .................................................... F16K 37/00
(52) U.S. Cl. .......................... 137/557; 137/552; 116/70; 128/202.22
(58) Field of Search .................................... 137/552, 557; 116/70; 128/202.22

(56) References Cited

U.S. PATENT DOCUMENTS

| | | | |
|---|---|---|---|
| 3,224,409 | * 12/1965 | Femger | 128/202.22 |
| 3,611,981 | 10/1971 | Warncke | 116/70 |
| 3,719,160 | * 3/1973 | Christianson | 116/70 |
| 3,785,333 | * 1/1974 | Warncke et al. | 116/70 |
| 3,811,400 | 5/1974 | Smilg | 116/70 |
| 4,064,899 | 12/1977 | Lehmann | 137/269 |
| 4,275,723 | 6/1981 | Warncke et al. | 128/202.22 |
| 4,350,115 | 9/1982 | Pasternack | 116/70 |
| 5,040,477 | * 8/1991 | Schiffmacher | 116/70 |
| 5,135,023 | * 8/1992 | Ross | 137/505.11 |

FOREIGN PATENT DOCUMENTS

| | | |
|---|---|---|
| 36 02 724 A1 | 8/1987 | (DE). |
| 195 16 485 A1 | 11/1996 | (DE). |
| WO 99/13945 | 3/1999 | (WO). |

* cited by examiner

Primary Examiner—A. Michael Chambers
Assistant Examiner—Thomas L. McShane
(74) Attorney, Agent, or Firm—Mark Kusner

(57) ABSTRACT

The invention provides an in-line low supply pressure alarm device preferably housed together with a gas pressure regulator and a gas flow controller, thereby eliminating the need for the operator to monitor gas availability. The alarm device is designed to be inserted in-line and includes a hollow housing with a gas inlet, a gas outlet, and an elongate internal chamber. A piston is disposed within the chamber for axial sliding between an alarm-on and an alarm-off position. The piston includes a piston head sealed in sliding engagement with an actuating compartment of the chamber. The actuating compartment of the chamber is filled with pressurized gas in flow communication with the gas inlet in operation. The piston includes an axially extending valve stem with a lateral alarm port in flow communication with the gas inlet. The valve stem is in sliding engagement with axially spaced apart seals defining an alarm plenum within the chamber. The alarm port of the valve stem is in flow communication with the alarm plenum when the piston is in the alarm-on position. A biasing spring engages the piston to bias the piston against the pressure of gas in the actuating compartment to the alarm-on position. The low pressure alarm is activated by a gas activated alarm in communication with the alarm plenum when low pressure is detected. Preferably the alarm port is aligned with a sealed compartment within the chamber when the piston is in the alarm-off position.

11 Claims, 2 Drawing Sheets

LOW SUPPLY PRESSURE ALARM FOR GAS SUPPLY

TECHNICAL FIELD

The invention is directed to a low supply pressure alarm to notify the operator of gas supply depletion and preferably integrally housed together with a gas regulator, and flow controller.

BACKGROUND OF THE ART

Breathable gas is administered to patients during medical treatment and often in emergency situations. Breathable gas is provided from compressed sources through mobile cylinders. Such devices are typically used in trauma situations by hospital and ambulance crews, firefighters, military medics, and the like during life threatening emergencies.

The pressure of breathable gas in cylinders is much higher than the pressure at which the breathable gas is administered to patients. In order to regulate the gas pressure during medical treatment, a gas pressure regulator is placed on gas cylinders. If the supply of breathable gas is depleted, the patient may suffer and devices driven by the gas pressure may cease to operate.

It is crucial for the operator of such devices to monitor the supply of gas. In the case of gas cylinders, the regulator generally includes a cylinder contents gauge which visually indicates the pressure remaining within the cylinder.

The operator of such devices is generally preoccupied with administering medication or providing other medical treatment during such emergency situations. However, the operator must maintain monitoring of the gas supply pressure to ensure that the patient receives a sufficient breathable gas supply. In the case of emergency medical treatment, small sized cylinders are generally carried in bags or cases to the emergency site. The regulator and gas pressure gauge mounted thereon are often not readily visible. Unfortunately, the monitoring of gas supply is a matter that can be easily overlooked in the crisis of an emergency medical situation.

Therefore, it is desirable to provide a low pressure alarm which relieves the operator of the burden of checking the input supply pressure to the regulator and ensure the presence of gas supply.

It is also desirable to provide an audible alarm indication of gas supply depletion to relieve the operator of the necessity of visually checking the cylinder contents gauge during an emergency situation.

DISCLOSURE OF THE INVENTION

The invention provides an in-line low supply pressure alarm device preferably housed together with a gas pressure regulator and a gas flow controller, thereby eliminating the need for the operator to monitor gas availability.

The alarm device is designed to be inserted in-line and includes a hollow housing with a gas inlet, a gas outlet, and an elongate internal chamber. There is only one moving part to reduce wear and maintenance, as well as to improve reliability. The piston is spring loaded to the alarm-on position and switches to trigger a gas flow through the alarm when the input gas pressure falls below a selected minimum pressure. The residual pressure in the supply system is sufficient to drive the alarm for a reasonable period of time thereby warning the operator before the gas supply completely expires.

In a commercial embodiment, the alarm device is housed together with a regulator and flow controller in a compact combined housing. The provision of a low cost input pressure alarm as part of a regulator/controller improves operation and reliability of the system and permits the introduction of a price premium as an upgraded high level regulator.

The pressure sensing piston is disposed within the chamber for axial sliding between the alarm-on and an alarm-off position depending on the pressure of gas acting on the piston head. The piston head is sealed in sliding engagement with an actuating compartment of the chamber. The actuating compartment of the chamber is filled with pressurised gas in flow communication with the gas inlet in operation.

The piston includes an axially extending valve stem with a lateral alarm port in flow communication with the gas inlet. The valve stem is in sliding engagement with axially spaced apart seals defining an alarm plenum within the chamber. The alarm port of the valve stem is in flow communication with the alarm plenum when the piston is in the alarm-on position. A biasing spring engages the piston to bias the piston against the pressure of gas in the actuating compartment to the alarm-on position.

The low pressure alarm is activated by a gas activated alarm device in communication with the alarm plenum when low pressure is detected. Preferably the alarm port is aligned with a sealed compartment within the chamber when the piston is in the alarm-off position to eliminate any leakage of high pressure gas that could possibly trigger a false alarm.

Further details of the invention and its advantages will be apparent from the detailed description and drawing included below.

BRIEF DESCRIPTION OF THE DRAWINGS

In order that the invention may be readily understood, one preferred embodiment of the invention will be described by way of example, with reference to the accompanying drawings wherein.

DETAILED DESCRIPTION OF PREFERRED EMBODIMENTS

Figure 1:
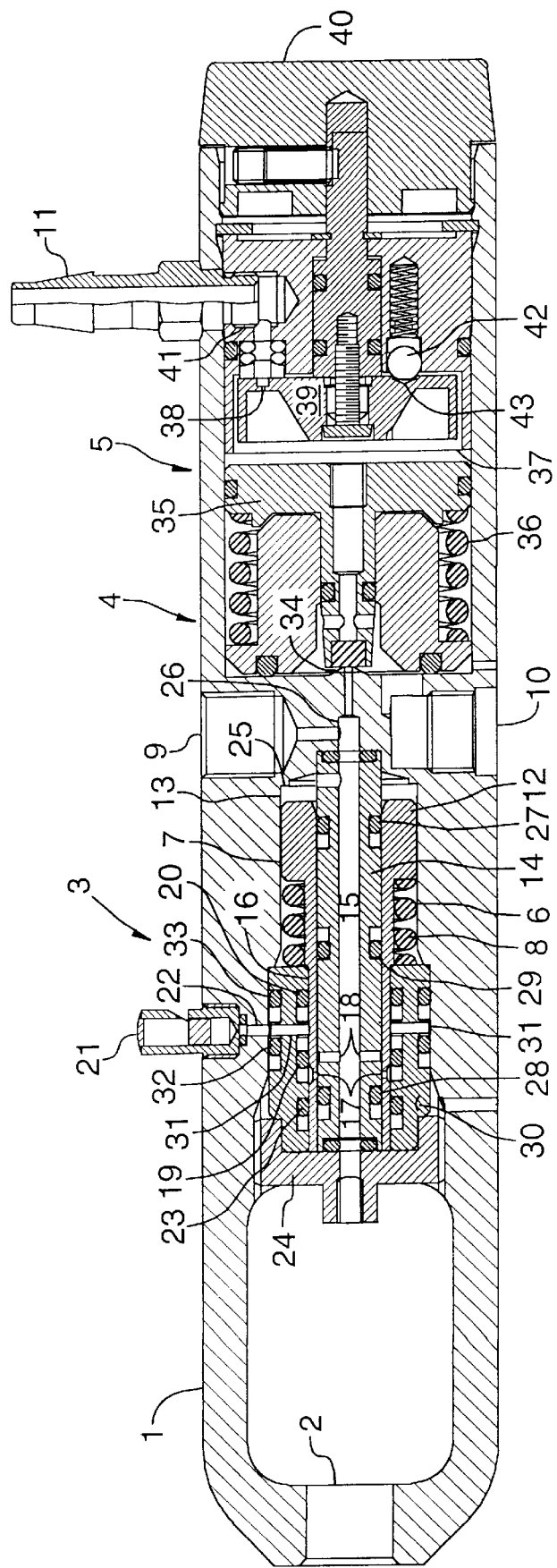
FIG. 1 is an axial cross-sectional view through a housing including an integral alarm in the alarm-off position, a gas pressure regulator and gas flow controller.

FIG. 1 shows a housing 1 within which all gas is conveyed axially from the gas inlet 2 through the inline low supply pressure alarm device 3, and optionally to the gas pressure regulator 4 or through the gas flow controller 5.

Figure 2:
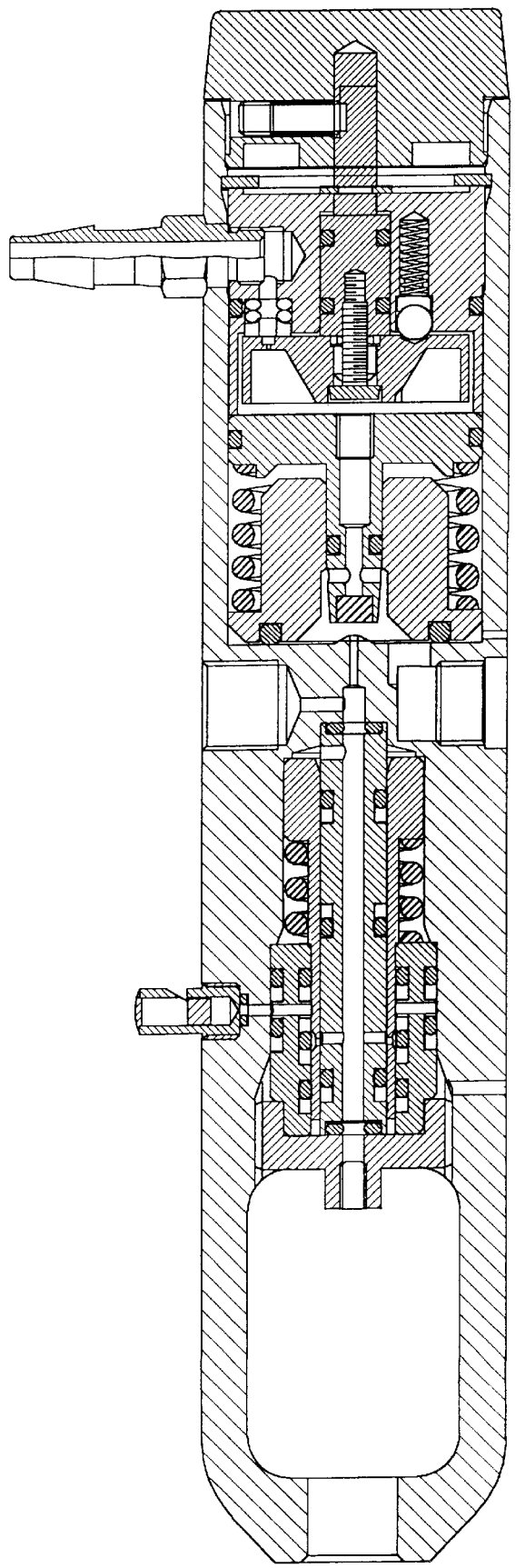
FIG. 2 is a like view with the alarm in the alarm-off position.

The hollow housing 1 has an elongate internal chamber within which a sliding piston 7 is disposed for axial sliding between an alarm-on position shown in FIG. 2 and an alarm-off position shown in FIG. 1.

Of the alarm device 3, the piston 7 and biasing spring 8 are the only moving parts.

Depending on the downstream equipment to be attached to the housing 1, the housing 1 includes a number of gas outlets as follows. Gas under high pressure flows from the gas inlet 2 through the centre of the alarm device 3 directly to a laterally extending high pressure outlet 9. No control over the pressure or quantity of flow is involved in the gas exiting from high pressure outlet 9. This high pressure outlet port 9 is provided for the attachment of a cylinder pressure monitoring gauge.

Gas flows axially through the regulator 4 and can pass through the regulated pressure outlet 10, however, at an unregulated rate of flow. If the quantity of flow and pressure are both to be regulated, gas that passes through the regulator 4 and flow controller 5 exits through flow regulated outlet 11 at a preselected flow quantity and pressure. Detailed operation of the pressure regulator 4 and the flow controller 5 are explained below after the following explanation of the gas alarm device 3.

The piston 7 includes a piston head 12 which is sealed in sliding engagement with the actuated compartment 13 of the chamber 6. The actuating compartment 13 is filled with pressurized gas in flow communication with the gas inlet 2. In the preferred embodiment illustrated, the piston 7 is mounted on a stationery core 14 surrounding an axial bore 15. The spring 6 biases the piston 7 against the pressure of the gas in the actuating compartment 13 towards the alarm-on position shown in FIG. 2. If the pressure of the gas in the actuating compartment 13 is above the preselected minimum pressure, then the resistance of the spring 8 is overcome and the piston 7 slides to the alarm-off position shown in FIG. 1.

The piston 7 includes an axially extending valve stem 16 with a lateral alarm port 17. In the alarm-on position shown in FIG. 2 the lateral core conduit 18 conveys gas from the bore 15 to the alarm port 17.

The valve stem 16 is housed in sliding engagement with axially spaced apart seals 19 and 20 which define an alarm plenum within the chamber 6. As can be appreciated, the components illustrated are precision machined to close tolerance.

However, there is a clearance between the moving parts such that an alarm plenum is provided between the seals 19 and 20. The close fit serves to restrict flow of high pressure gas and reduce the pressure of gas through the alarm 21. As shown in FIG. 2, the alarm port 17 of the valve stem 16 is in flow communication with the alarm plenum when the piston 7 is in the alarm-on position.

A gas activated alarm 21 such as an audible reed alarm or whistle is in direct communication with the alarm plenum between seals 19 and 20 via conduit 22. When the piston 7 is in the alarm-off position shown in FIG. 1, the alarm port 17 is aligned with a sealed compartment defined within the chamber between seals 19 and 23. Therefore, in the alarm-off position shown in FIG. 1, the sufficiently high pressure within the actuating compartment 13 moves the piston and alarm port 17 to a position within the sealed compartment defined by seals 23 and 19, and as a result gas conducting through the lateral core conduit 18 and alarm port 17 cannot escape. The potential for false alarms is thereby minimized.

Minimal movement of the piston 7 is desirable to ensure long life for the various seals and to ensure precise operation. The chamber 6 includes means for limiting the travel of the piston 7 to positively locate the piston in the alarm-on position and in the alarm-off position. In the alarm-off position shown in FIG. 1, the end of the stem 16 positively engages the inner face of threaded cap 24 which encloses the alarm device 3 within the chamber 6. In the alarm-on position shown in FIG. 2, the piston head 12 positively engages a shoulder abutment 25 extending into the actuating compartment 13. All gas outlets 9, 10 and 11 are fed by a bore 26 which extends from the bore 15 and communicates with the actuating compartment 13.

To provide simple installation and maintenance, all high pressure seals are mounted in an accessible manner as follows. The core 14 includes a seal 27 to prevent leakage of gas from the actuating compartment 13 between the piston 7 and core 14. As well, seals 28 and 29 prevent leakage from the lateral core conduit 18. Seals 27, 28 and 29 may be easily inspected and maintained by removing the cap 24 and core 14. On the radially outward sides of the piston 7, seals 20, 19 and 23 are housed within a sealing sleeve 30 disposed between the valve stem 16 and the walls of the chamber 6. The sleeve 30 includes a lateral sleeve conduit 31, between the alarm plenum defined between seals 19 and 20 and the gas activated alarm 21. To prevent leakage between the sleeve 30 and the chamber walls 6, seals 32 and 33 are provided on each side of the lateral sleeve conduit 31.

Since all gas within the alarm device 3 is at extremely high pressure, the provision of these seals in an easily accessible and simply manufactured manner is essential to prevent catastrophic failure. As a result therefore, the mounting of seals in the core 14 and sealing sleeve 30 is of significant advantage. Particularly, where seals are mounted together with anti-blowout rings in a rectangular shaped recess, the installation of seals and rings is simplified since the sleeve 30 can be removed from the housing 1 for complete access.

Gas exiting through the bore 26 can pass through the high pressure outlet 9 bypassing the regulator 4 and flow controller 5 if desired.

Gas with pressure regulated passes through bore 26 to the regulator through volcano valve seat 34. The regulator piston 35 moves axially against the biasing force of regulator spring 36 in response to pressure of gas accumulating within the regulator plenum 37. As a result, the flow of gas through the valve seat 34 and out regulated pressure outlet 10 is determined by the axial movement of the regulator piston 35 as it constricts the flow of gas through valve seat 34.

If further control over the pressure and flow of gas is required, outlet 11 is provided whereby gas passes through different sized orifices 38 in a flow controlling disk 39. Manually rotating the knob 40 rotates the disk 39 between various sized orifices 38 which will align with the exit nozzle 41.

Spring loaded ball 42 is provided to rest in aligned sockets 43 in the flow disk 39 to positively locate and align the orifices 38 and exit nozzle 41. By precisely drilling the size of orifices 38 different sized orifices 38 can be preset for a known flow and pressure result.

By providing a single housing 1 with integrally combined alarm 3 and pressure regulator 4 with gas flow controller 5, a single regulator can be manufactured wherein gas flowing out of high pressure outlet 9, the regulator pressure outlet 10 or flow and pressure regulated outlet 11 can be monitored such that an alarm is sounded when pressure from the supply drops below a preselected minimum pressure.

For simple installation and maintenance, all high pressure seals are mounted on a removable sleeve 30 and removable core 14. The only moving parts of the alarm device are the piston 7 and spring 8 for improved reliability and reduced wear.

Although the above description and accompanying drawings relate to a specific preferred embodiment as presently contemplated by the inventors, it will be understood that the invention in its broad aspect includes mechanical and functional equivalents of the elements described and illustrated.

What is claimed is:

1. An in-line low supply pressure alarm device comprising:
   a hollow housing with a gas inlet, a gas outlet, and an elongate internal chamber;
   a piston disposed within the chamber for axial sliding between an alarm-on and an alarm-off position, the piston including a piston head sealed in sliding engagement with an actuating compartment of the chamber, the actuating compartment of the chamber being filled with pressurised gas in flow communication with the gas inlet, the piston including an axially extending valve stem with a lateral alarm port in flow communication with the gas inlet, the valve stem in sliding engagement with axially spaced apart seals defining an alarm plenum within the chamber, the alarm port of the valve stem being in flow communication with the alarm plenum when the piston is in the alarm-on position;

biasing means engaging the piston for biasing the piston against the pressure of gas in the actuating compartment to the alarm-on position;

a gas activated alarm in communication with the alarm plenum;

wherein the gas inlet is in flow communication with the actuating compartment via an axial bore extending through the piston, and wherein the lateral alarm port is in flow communication with the axial bore; and wherein the piston is mounted on a stationary core surrounding said axial bore, the core including a lateral core conduit between axially spaced apart sliding seals defining a core plenum, the alarm port of the stem being disposed within the core plenum in the alarm-on and in the alarm-off positions.

2. An alarm device according to claim 1 wherein the alarm port is aligned with a sealed compartment within the chamber when the piston is in the alarm-off position.

3. An alarm device according to claim 1 wherein the chamber includes limiting means in the chamber for limiting the travel of the piston in the alarm-on position and in the alarm-off position.

4. An alarm device according to claim 3 wherein the limiting means comprise end abutments axially disposed a selected axial distance from the piston.

5. An alarm device according to claim 1 wherein the gas outlet extends from the actuating compartment.

6. An alarm device according to claim 1 comprising a sealing sleeve disposed between the stem and chamber, the sleeve including a lateral sleeve conduit between the alarm plenum and the gas activated alarm.

7. An alarm device according to claim 6 wherein the alarm port is aligned with a sealed compartment within the sleeve when the piston is in the alarm-off position.

8. An alarm device according to claim 1 wherein the gas activated alarm is activated by gas flow.

9. An alarm device according to claim 8 wherein the gas activated alarm is selected from the group consisting of: an audible reed alarm; and a whistle.

10. An alarm device according to claim 1 including a gas pressure regulator within the housing having a regulator intake in flow communication with the gas outlet and a pressure regulated output.

11. An alarm device according to claim 10 including a gas flow controller within the housing and in flow communication with the output of the pressure regulator.

* * * * *